United States Patent [19]

Kramer

[11] E Patent Number: Re. 33,080

[45] Reissued Date of Patent: Oct. 3, 1989

[54] ADAMANTANE CATALYZED PARAFFIN ISOMERIZATION

[75] Inventor: George M. Kramer, Berkeley Heights, N.J.

[73] Assignee: Exxon Research and Engineering Company, Florham Park, N.J.

[21] Appl. No.: 896,229

[22] Filed: Aug. 14, 1986

Related U.S. Patent Documents

Reissue of:

[64] Patent No.: 4,357,483
Issued: Nov. 2, 1982
Appl. No.: 298,117
Filed: Aug. 31, 1981

U.S. Applications:

[63] Continuation of Ser. No. 630,440, Jul. 13, 1984, abandoned.

[51] Int. Cl.[4] ..... C07C 5/13

[52] U.S. Cl. ..... 585/740; 585/741; 585/743; 585/745; 585/746; 585/747; 585/749

[58] Field of Search ..... 585/740, 741, 743, 745, 585/746, 747, 749

[56] References Cited

U.S. PATENT DOCUMENTS

| | | | |
|---|---|---|---|
| 2,468,746 | 5/1949 | Greenfelder et al. | 585/745 |
| 2,475,358 | 7/1949 | Moore et al. | 585/737 |
| 2,965,693 | 12/1960 | Kramer | 260/683.53 |
| 3,231,633 | 1/1966 | Kramer | 260/683.61 |
| 3,310,469 | 3/1967 | Paulshock et al. | 167/65 |
| 3,324,196 | 6/1967 | Kramer et al. | 260/683.51 |
| 3,328,251 | 6/1967 | Smith | 167/65 |
| 3,364,280 | 1/1968 | Kramer | 260/683.51 |
| 3,365,515 | 1/1968 | Petty et al. | 260/683.63 |
| 3,382,288 | 5/1968 | Schneider | 260/666 |
| 3,391,220 | 7/1968 | Haensel | 260/683.76 |
| 3,408,419 | 10/1968 | Herbert et al. | 250/683.51 |
| 3,546,308 | 12/1970 | Moore | 268/666 |
| 3,551,514 | 12/1970 | Evering | 260/683.59 |
| 3,594,445 | 7/1971 | Parker | 260/683.68 |
| 3,617,516 | 2/1972 | Van Gooswilligen et al. | 208/134 |
| 3,671,598 | 6/1972 | Moore | 260/666 M |
| 3,674,681 | 7/1972 | Lyon | 208/141 |
| 3,689,590 | 9/1972 | Rakow et al. | 260/683.63 |
| 3,705,194 | 12/1972 | Scherm et al. | 260/561 A |
| 3,725,500 | 4/1973 | Kramer | 260/683.68 |
| 3,766,286 | 10/1973 | Olah | 260/668 A |
| 3,803,263 | 4/1974 | Schneider et al. | 260/683.76 |
| 3,829,525 | 8/1974 | Cole et al. | 260/683.63 |
| 3,839,487 | 10/1974 | Clonts | 260/683.48 |
| 3,839,490 | 10/1974 | Schneider | 260/683.76 |
| 3,852,371 | 12/1974 | Kemp | 260/683.47 |
| 3,855,294 | 12/1974 | Podesva et al. | 260/570 R |
| 3,862,231 | 1/1975 | Podesva et al. | 260/570 R |
| 3,862,987 | 1/1975 | Podesva et al. | 260/570.6 |
| 3,865,896 | 2/1975 | McCoy et al. | 260/683.51 |
| 3,867,476 | 2/1975 | Torck | 260/683.68 |
| 3,870,765 | 3/1975 | McCoy et al. | 260/683.51 |
| 3,879,489 | 4/1975 | Yurchak et al. | 260/683.44 |
| 3,880,945 | 4/1975 | Kramer et al. | 260/683.75 |
| 3,926,839 | 12/1975 | McCoy et al. | 252/355 |
| 4,022,847 | 5/1977 | McClure | 260/683.68 |
| 4,025,577 | 5/1977 | Siskin et al. | 260/683.51 |
| 4,048,251 | 9/1977 | Cohn et al. | 260/683.68 |
| 4,058,575 | 11/1977 | Cohn et al. | 260/666 |
| 4,162,233 | 7/1979 | Kramer | 252/429 |
| 4,179,402 | 12/1979 | Kim et al. | 252/431 |
| 4,210,647 | 7/1980 | DeLong | 424/250 |
| 4,229,611 | 10/1980 | Kramer | 585/728 |
| 4,271,162 | 6/1981 | DeLong | 424/250 |
| 4,273,774 | 6/1981 | Scherm | 424/253 |
| 4,346,112 | 8/1982 | Henkel et al. | 424/325 |
| 4,357,483 | 11/1982 | Kramer | 585/740 |
| 4,357,484 | 11/1982 | Kramer | 585/740 |
| 4,400,571 | 8/1983 | Robinson | |

OTHER PUBLICATIONS

Olah, *Friedel-Crafts & Related Reactions*, vol. I, pp. 201-203 & 283-286, John Wiley & Sons, N.Y. 1963.

"Industrial Laboratory Alkylation", edited by Lyle F. Albright and Arthur R. Goldsby, ACS Symposium Series 55, published Washington, D.C., 1977, Chapter One, Alkylation Studies by George M. Kramer.

J. Org. Chem. 44, pp. 2619-2624 (1979) by D. Mirda, D. Rapp and G. M. Kramer.

J. Amer. Chem. Soc. 98, pp. 5864-5870 (1976) by P. Van Pelt and H. M. Buck.

Studies in Organic Chemistry, vol. 5, "Adamantane, the Chemistry of Diamond Molecules", R. C. Fort, Jr., Marcel Dekker, Inc., New York (1976), pp. 75-111 and 127-141.

*Primary Examiner*—Curtis R. Davis

*Attorney, Agent, or Firm*—Henry E. Naylor; Joseph J. Dvorak

[57] ABSTRACT

A process is described for non-cyclic paraffin isomerization under strong acid conditions in which an adamantane hydrocarbon is used to substantially increase the reaction rate of the isomerization.

11 Claims, No Drawings

ADAMANTANE CATALYZED PARAFFIN ISOMERIZATION

Matter enclosed in heavy brackets [ ] appears in the original patent but forms no part of this reissue specification; matter printed in italics indicates the additions made by reissue.

*This application is a continuation of application Ser. No. 630,440, filed July 13, 1984, and now abandoned, which is a reissue of U.S. Pat. No. 4,357,484, issued Nov. 2, 1982.*

BACKGROUND OF THE INVENTION

This invention relates to a catalytic process for paraffin isomerization producing branched paraffin isomers under strong acid catalyzed conditions and in the presence of adamantane hydrocarbons as hydride transfer catalysts.

Isobutane-olefin alkylation or paraffin isomerization under strong acid conditions are well-known processes for producing a wide variety of useful hydrocarbon materials and particularly gasoline additives. For example, trimethylpentanes, which can be produced by alkylating isobutylene with isobutane in sulfuric acid or liquid HF, are commonly used for blending for gasoline octane improvement. An example of an acid catalyzed reaction process is described in U.S. Pat. No. 3,231,633.

Hydrocarbon conversion processes employing novel Lewis acid systems are disclosed in U.S. Pat. Nos. 4,229,611 and 4,162,333, both assigned to Exxon Research and Engineering Company.

U.S. Pat. No. 3,671,598 describes a process for isomerizing saturated cyclic hydrocarbons under strong acid conditions in the presence of an adamantane hydrocarbon. However, no suggestion is made that a similar system might be useful for isomerizing paraffinic hydrocarbons.

New methods for producing such branched paraffinic hydrocarbons are constantly being searched for in an effort to increase selectivity yield, and reaction rate, and decrease the cost of said process.

SUMMARY OF THE INVENTION

We have unexpectedly found that the presence of an adamantane hydrocarbon in a strong acid system containing a paraffinic hydrocarbon rapidly increases the rate of isomerization of said hydrocarbon, presumably through increased intermolecular hydride transfer that the paraffin undergoes in the system. Since intermolecular hydride transfer is often the rate-determining step in paraffin isomerization (see "Industrial Laboratory Alkylation" edited by Lyle F. Albright and Arthur R. Goldsby, ACS Symposium Series 55, published Washington, D.C., 1977, Chapter One, "Alkylation Studies" by G. M. Kramer), then the presence of the adamantane hydrocarbon will serve to significantly increase the reaction rate of such an isomerization process. In the production of octane-increasing agents, this should lead to the promotion of purer product quality due to higher selectivity, lower acid consumption, which is an evironmental consideration, and higher yields, which enhances the economics of the process.

More specifically, by this invention there is provided an isomerization process comprising contacting a $C_4$–$C_6$ non-cyclic aliphatic or paraffinic hydrocarbon with a strong acid system in the presence of an adamantane hydrocarbon containing at least one unsubstituted bridgehead position, at a temperature of about −100° to 150° C., thereby producing a branched isomer of said paraffinic hydrocarbon.

In the process, the total described range of applicable paraffins can be used in the subject isomerization process, under very strong acid conditions, e.g. $AlBr_3$. However, in the slightly weaker acid systems, such as $H_2SO_4$ and HF, n-paraffins like n-butane do not generally undergo this isomerization process and they require the stronger acid systems described herein.

DESCRIPTION OF THE INVENTION AND PREFERRED EMBODIMENTS

The reason that the adamantane hydrocarbon serves to increase the rate of intermolecular hydride transfer during paraffin isomerization, involving aliphatic species, is not clearly understood. One theory that we do not wish to be bound by is that reversible hydride transfer between adamantane and carbonium ions in solution is enhanced due to the lack of steric repulsions in the transition state involving adamantane during the process compared to that involving a paraffinic hydrocarbon.

In the process $C_4$–$C_6$ non-cyclic paraffinic hydrocarbons are isomerized. Preferably, the paraffinic hydrocarbon is a component of a readily available refinery stream. Representative examples of operable paraffins include 3-methylpentane, 2-methylpentane, n-hexane, n-pentane, n-butane, and the like, and isomers and mixtures thereof.

The above-described paraffins in the process can be converted to their carbonium ions which then isomerize, by reaction with the adamantyl cation. The latter forms readily when adamantane is added to a strong acid already containing alkyl carbonium ions or it can be formed by solvolysis of an adamantyl halide.

The product paraffinic hydrocarbons in the process are $C_4$–$C_6$ branched paraffinic hydrocarbons and are useful as gasoline blending compounds for octane improvement and as hydrocarbon solvents. Representative examples include isobutane, isopentane, 2-methylpentane, 3-methylpentane, 2,3-dimethylbutane, 2,2-dimethylbutane, and the like. Preferred product paraffinic hydrocarbons in the process are the most highly branched isomers in each carbon number, e.g. isopentane, dimethylbutanes, and isobutane, (except for neopentane, which is not obtained in these reactions).

The phrase "a strong acid system", as used herein, refers to the acid system capable of assisting in generating carbonium ions in the process and includes an "acid component" and a solvent, or one material that can function in both capacities, such as concentrated sulfuric acid or liquid HF. The acid system can be liquid, solid, vapor or gaseous. Preferred is a liquid acid system.

The strong acid components in the acid system are conventional protic, aprotic or Lewis acids and include $AlBr_3$, $AlCl_3$, $GaCl_3$, $TaF_5$, $SbF_5$, $AsF_5$, $Bf_3$, HF, HCl, HBr, $H_2SO_4$, $HSO_3F$, $CF_3SO_3H$, and the like and mixtures thereof. Preferred are $AlCl_3$, $AlBr_3$, $GaCl_3$ and $TaF_5$.

Also a component of the "acid system", if required, is a solvent for the acid component. For Lewis acids, halogenated paraffins and aromatics are generally used; representative examples include $CH_3Br$, $CH_2Br_2$, $CH_2Cl_2$, 1,2-dichloroethane, 1,2,3-trichlorobenzene, 1,2,3,4-tetrachlorobenzene, pentafluorobenzene, HF, $H_2SO_4$, $HSO_3F$, $CF_3SO_3H$, and the like and mixtures thereof.

The molar concentration of acid component in the solvent, if they are different materials, is generally between 0.1 and 8.0 M, and preferably 0.5 to 4.0 M (moles/liter).

The volume ratio of the acid system to the paraffinic hydrocarbon to be isomerized is generally about 5/1 to 1/5 and preferably 3/1 to 1/3. However, larger and smaller ratios can be effectively employed.

The adamantane hydrocarbon useful in the process contains at least one unsubstituted bridgehead position and can be prepared by conventional methods in the art. It is believed that at least one bridgehead adamantane position must be unubstituted in order for an increase in intermolecular hydride transfer to occur. The adamantyl ring can be substituted with alkyl groups, which are generally linear or branched $C_1$–$C_4$ alkyl being methyl, ethyl, n-propyl, isopropyl, n-butyl, isobutyl, 1-butyl, and the like. A preferred alkyl substituent, if present, is methyl.

Representative adamantane hydrocarbons in the process are adamantane, 1-methyladamantane, 2-methyladamantane, 1,3-dimethyladamantane, and the like. Preferably, unsubstituted adamantane is used.

The molar concentration of the adamantane hydrocarbon in solution in the paraffinic hydrocarbon in the process ranges from about 0.1 M to 1.0 M (moles/liter). However, larger and smaller ratios can also be used effectively.

Temperatures in the process are conducted in the range of about −100° to 150° C. and preferably −50° to 100° C.

The process is normally carried out at atmospheric pressure but may also be conducted at higher pressures up to about 20 atmospheres.

Yields of isomerized paraffinic branched hydrocarbons in the process are in the range of 80 to 100 percent of theory, based on starting paraffin.

Particularly preferred embodiments of the subject process are where refinery butane, pentane or hexane streams which are not equilibrium are isomerized to isobutane, isopentane and equilibrium mixtures of $C_6$ isomers.

Apparatus for carrying out the subject process is conventional either in a laboratory, pilot plant, or full industrial scale and the process can be conducted in a batch-type operation or in a continuous-type operation and in slurry, liquid, gaseous, or vapor phase. Preferred type of process is a continuous operation.

Generally, the process is conducted by contacting a liquid mixture of paraffin and adamantane hydrocarbon with the acid system described herein. If the hydrocarbon mixture is miscible with said acid system, then the reaction takes place in a one-phase homogeneous manner. If the acid system is, for example, $H_2SO_4$, then the process is conducted in a two-phase manner, the acid system being the lower phase. The entire system is preferably at reaction temperature at time of mixing during which the entire system is adequately mixed, stirred and agitated to insure good contact between the acid system and the hydrocarbon system. The reaction is allowed to progress until a desired or substantial quantity of formed product is obtained. This can be monitored by analytical methods such as gas chromatography and mass spectrometry. After the desired paraffinic product has been formed, the phases can be separated and the hydrocarbon phase treated by extraction or fractional distillation, and the like, to separate out and collect the desired product.

Particularly preferred embodiments of the process are where n-butane is isomerized to isobutane; where n-pentane is isomerized to isopentane; where n-hexane is isomerized to a mixture of $C_6$ isomers, containing preferably more than 20 percent 2,2-dimethylbutane.

It is to be understood that obvious modification and variations on the above-described procedure and subject process not specifically described herein, are deemed to be encompassed within the general scope and spirit of this application.

The following example is illustrative of the best mode of carrying out the invention, as contemplated by me, and should not be construed as being limitations on the scope or spirit of the instant invention.

EXAMPLE

This example demonstrates the ability of adamantane to catalyze an isomerization reaction in sulfuric acid. One hundred ml. of conc. $H_2SO_4$, (96%) was mixed with one hundred ml. of 3-methylpentane in a 500 ml. 2-neck flask at room temperature. The system was stirred vigorously and samples of the hydrocarbon phase were withdrawn periodically and analyzed by gas chromatography for the extent of isomerization. The reaction was then repeated with 0.1 M and 0.3 M solutions of adamantane in 3-methylpentane. The relative isomerization rates in the systems were; blank: 0.1 M:0.3 M = 1:1.56:2.64. Thus, the net isomerization rate of 3-methylpentane to 2-methylpentane more than doubled with the 0.3 M solution, as compared to the control blank.

What is claimed is:

1. An isomerization process comprising contacting a $C_4$–$C_6$ non-cyclic paraffinic hydrocarbon with a strong acid system *selected from HBr, HF, HCl, $H_2SO_4$, $HSO_3F$, $CF_3SO_3H$ and mixture thereof* in the presence of an adamantane hydrocarbon containing at least one unsubstituted bridgehead position, *wherein the molar concentration of the adamantane hydrocarbon in solution in the paraffin hydrocarbon is from about 0.1M to 1M* at a temperature of about −100° to 150° C., thereby producing a branched isomer of said paraffinic hydrocarbon.

2. The process of claim 1 wherein said paraffinic hydrocarbon is selected from n-butane, n-pentane, n-hexane, 2-methylpentane, 3-methylpentane isomers thereof, and mixtures thereof.

[3. The process of claim 1 wherein said acid system contains an acid component selected from $AlCl_3$, $AlBr_3$, $GaCl_3$, $TaF_5$, $SbF_5$, $AsF_5$, $BF_3$, HBr, HF, HCl, $H_2SO_4$, $HSO_3F$, $CF_3SO_3H$, and mixtures thereof.]

4. The process of claim [3] *1* wherein said acid system further contains a solvent selected from $CH_3Br$, $CH_2Br_2$, $CH_2Cl_2$, 1,2-dichloroethane, 1,2,3-trichlorobenzene, 1,2,3,4-tetrachlorobenzene, pentafluorobenzene; HF, $H_2SO_4$, $HSO_3F$, $CF_3SO_3H$, and mixtures thereof.

5. The process of claim 1 wherein said adamantane hydrocarbon is unsubstituted adamantane.

6. The process of claim 1 wherein said temperature is in the range of about −50° to 100° C.

7. The process of claim 1 being conducted in a continuous manner.

8. The process of claim 1 wherein said paraffin is 3-methylpentane and said product is 2-methylpentane.

[9. The process of claim 3 wherein said strong acid system contains $AlCl_3$, $AlBr_3$, $GaCl_3$ or $TaF_5$.]

10. The process of claim 1 wherein said paraffin is n-butane and said product is isobutane.

11. The process of claim 1 wherein said paraffin is n-pentane and said product is isopentane.

12. The process of claim 1 wherein said paraffin is n-hexane and said product is a mixture of $C_6$ isomers containing more than 20 weight percent 2.2-dimethylbutane.

13. The process of claim 1 wherein said paraffin is a mixture of $C_4$, $C_5$ or $C_6$ isomers wherein at least one fraction is not at thermodynamic equilibrium.

* * * * *